United States Patent
Ghorbanian et al.

(10) Patent No.: US 10,433,753 B2
(45) Date of Patent: Oct. 8, 2019

(54) STOCHASTIC OSCILLATOR ANALYSIS IN NEURO DIAGNOSTICS

(71) Applicant: Cerora, Inc., Yardley, PA (US)

(72) Inventors: Parham Ghorbanian, Wayne, PA (US);
Hashem Ashrafiuon, Wayne, PA (US);
Adam J. Simon, Yardley, PA (US)

(73) Assignee: Cerora, Inc., Yardley, PA (US)

( * ) Notice: Subject to any disclaimer, the term of this patent is extended or adjusted under 35 U.S.C. 154(b) by 20 days.

(21) Appl. No.: 15/302,535

(22) PCT Filed: Apr. 7, 2015

(86) PCT No.: PCT/US2015/024672
§ 371 (c)(1),
(2) Date: Oct. 7, 2016

(87) PCT Pub. No.: WO2015/157253
PCT Pub. Date: Oct. 15, 2015

(65) Prior Publication Data
US 2017/0032098 A1 Feb. 2, 2017

Related U.S. Application Data

(60) Provisional application No. 61/976,318, filed on Apr. 7, 2014.

(51) Int. Cl.
*A61B 5/04* (2006.01)
*A61B 5/0476* (2006.01)
(Continued)

(52) U.S. Cl.
CPC .......... *A61B 5/0476* (2013.01); *A61B 5/0484* (2013.01); *A61B 5/4088* (2013.01);
(Continued)

(58) Field of Classification Search
CPC ....... G06F 19/00; G06F 19/3437; A61B 5/00; A61B 5/0476; A61B 5/7264;
(Continued)

(56) References Cited

U.S. PATENT DOCUMENTS 6,463,371 B1  10/2002  Ulyanov et al.
2005/0215889 A1  9/2005  Patterson, II
(Continued)

FOREIGN PATENT DOCUMENTS

WO  WO 2011/075697 A2  6/2011
WO  WO-2015157253 A1  10/2015

OTHER PUBLICATIONS

"International Application Serial No. PCT/US2015/024672, International Preliminary Report on Patentability dated Oct. 20, 2016", 9 pgs.

(Continued)

*Primary Examiner* — Eric J Messersmith
(74) *Attorney, Agent, or Firm* — Schwegman Lundberg & Woessner, P.A.

(57) ABSTRACT

A system and method for modeling bio-signals in the form of non-linear stochastic oscillators by extracting time series data from a subject into a series of summary fit parameters and comparing the unknown fit parameters to a set of normative fit parameters to determine whether the subject should be included in a group or not. The method includes data collection, feature extraction and then comparison of fit parameters from a non-linear stochastic oscillator model to a normative standard to make the in or out determination for a particular group. The system includes a processor programmed to perform the steps of the method.

13 Claims, 2 Drawing Sheets

(51) Int. Cl.
    *A61B 5/00*      (2006.01)
    *A61B 5/0484*    (2006.01)
    *G16H 50/50*     (2018.01)

(52) U.S. Cl.
    CPC .......... *A61B 5/7264* (2013.01); *A61B 5/7275* (2013.01); *A61B 5/7278* (2013.01); *A61B 5/7282* (2013.01); *G16H 50/50* (2018.01)

(58) Field of Classification Search
    CPC ... A61B 5/0484; A61B 5/7275; A61B 5/7278; A61B 5/4088; A61B 5/7282; G16H 50/50
    See application file for complete search history.

(56) References Cited

U.S. PATENT DOCUMENTS

2010/0292752 A1   11/2010   Bardakjian et al.
2010/0302270 A1   12/2010   Echauz et al.

OTHER PUBLICATIONS

"International Application Serial No. PCT/US2015/024672, International Search Report dated Jul. 16, 2015", 2 pgs.
"International Application Serial No. PCT/US2015/024672, Written Opinion dated Jul. 16, 2015", 7 pgs.

Fig. 1

STOCHASTIC OSCILLATOR ANALYSIS IN NEURO DIAGNOSTICS

CROSS REFERENCE TO RELATED APPLICATIONS

This application is a National Stage Application filed under 35 U.S.C. § 371 of International Application No. PCT/US2015/024672, filed Apr. 7, 2015, which claims benefit of Provisional Application No. 61/976,318, filed Apr. 7, 2014. The contents of both patent applications are hereby incorporated by reference in their entireties.

TECHNICAL FIELD

The invention relates to diagnosis and analysis of brain health through the use of activated tasks and stimuli in a system to dynamically assess one's brain state and function.

BACKGROUND

Normal functioning of the brain and central nervous system is critical to a healthy, enjoyable and productive life. Disorders of the brain and central nervous system are among the most dreaded of diseases. Many neurological disorders such as stroke, Alzheimer's disease, and Parkinson's disease are insidious and progressive, becoming more common with increasing age. Others such as schizophrenia, depression, multiple sclerosis and epilepsy arise at younger age and can persist and progress throughout an individual's lifetime. Sudden catastrophic damage to the nervous system, such as brain trauma, infections and intoxications can also affect any individual of any age at any time.

Most nervous system dysfunction arises from complex interactions between an individual's genotype, environment and personal habits and thus often presents in highly personalized ways. However, despite the emerging importance of preventative health care, convenient means for objectively assessing the health of one's own nervous system have not been widely available. Therefore, new ways to monitor the health status of the brain and nervous system are needed for normal health surveillance, early diagnosis of dysfunction, tracking of disease progression and the discovery and optimization of treatments and new therapies.

Unlike cardiovascular and metabolic disorders, where personalized health monitoring biomarkers such as blood pressure, cholesterol, and blood glucose have long become household terms, no such convenient biomarkers of brain and nervous system health exist. Quantitative neurophysiological assessment approaches such as positron emission tomography (PET), functional magnetic resonance imaging (fMRI) and neuropsychiatric or cognition testing involve significant operator expertise, inpatient or clinic-based testing and significant time and expense. One potential technique that may be adapted to serve a broader role as a facile biomarker of nervous system function is a multi-modal assessment of the brain from a number of different forms of data, including electroencephalography (EEG), which measures the brain's ability to generate and transmit electrical signals. However, formal lab-based EEG approaches typically require significant operator training, cumbersome equipment, and are used primarily to test for epilepsy.

Alternate and innovative biomarker approaches are needed to provide quantitative measurements of personal brain health that could greatly improve the prevention, diagnosis and treatment of neurological and psychiatric disorders. Unique multi-modal devices and tests that lead to biomarkers of Parkinson's disease, Alzheimer's disease, concussion and other neurological and neuropsychiatric conditions is a pressing need.

SUMMARY

The present invention addresses the needs in the art by providing a system and method for modeling bio-signals in the form of non-linear stochastic oscillators by extracting time series data from a subject into a series of summary fit parameters and comparing the unknown fit parameters to a set of normative fit parameters to determine whether the subject should be included in a group or not. The method includes data collection, feature extraction and then comparison of fit parameters from the non-linear stochastic oscillator model to a normative standard to make the in or out determination for a particular group. The system includes a processor programmed to perform the steps of the method.

In exemplary embodiments, the method models bio-signals in the form of non-linear stochastic oscillators by performing the steps of collecting bio-signal data from a subject as time series data, extracting features from the collected bio-signal data using a non-linear stochastic oscillator model to provide a series of summary fit parameters, and comparing unknown fit parameters from the series of summary fit parameters to a set of normative fit parameters to determine whether the subject should be included in a group corresponding to the normative fit parameters or not.

In the exemplary embodiments, the non-linear stochastic oscillator model is a Duffing-van der Pol oscillator model and the collected bio-signal data comprises dynamics of EEG collected from the subject. The normative fit parameters may correspond to values of k1, k2, b1, b2, epsilon1, epsilon2, and mu for normal control subjects and/or for control subjects having a disease or injury state. For example, the control subjects may be a population of individuals having Alzheimer's disease.

In the exemplary embodiments, determining whether the subject should be included in a group corresponding to the normative fit parameters or not comprises determining if the unknown fit parameters from the subject are within a confidence interval of the normative fit parameters and, if so, then determining that the unknown fit parameters are within a biological variation of normal for the normative fit parameters and, if not, then determining that the unknown fit parameters are outside the biological variation of normal for the normative fit parameters. Also, if the unknown fit parameters are determined to be between a control state and a first state, the method includes the step of creating signatures that are weighted equally across the normative fit parameters, not weighted, or that counts a number of parameters that are within a distance of a pole.

The invention also includes a system for implementing such a method. In particular, the invention includes a system including a memory that stores software instructions and a processor that processes the software instructions to determine whether a subject has characteristics consistent with a normal state or an injury or disease state by collecting bio-signal data from the subject as time series data, extracting features from the collected bio-signal data using a non-linear stochastic oscillator model to provide a series of summary fit parameters, and comparing unknown fit parameters from the series of summary fit parameters to a set of normative fit parameters to determine whether the subject is within or outside a normal state for the normative fit parameters.

In exemplary embodiments, the processor further processes software instructions to implement the step of determining that the subject is within a normal state for fit parameters corresponding to an injury or disease state, such as Alzheimer's disease.

BRIEF DESCRIPTION OF THE DRAWINGS

Embodiments of the invention can be better understood with reference to the following drawings.

DETAILED DESCRIPTION OF ILLUSTRATIVE EMBODIMENTS

The invention will be described in detail below with reference to FIGS. 1-2. Those skilled in the art will appreciate that the description given herein with respect to those figures is for exemplary purposes only and is not intended in any way to limit the scope of the invention. All questions regarding the scope of the invention may be resolved by referring to the appended claims.

Definitions

By "electrode to the scalp" we mean to include, without limitation, those electrodes requiring gel, dry electrode sensors, contactless sensors and any other means of measuring the electrical potential or apparent electrical induced potential by electromagnetic means.

By "monitor the brain and nervous system" we mean to include, without limitation, surveillance of normal health and aging, the early detection and monitoring of brain dysfunction, monitoring of brain injury and recovery, monitoring disease onset, progression and response to therapy, for the discovery and optimization of treatment and drug therapies, including without limitation, monitoring investigational compounds and registered pharmaceutical agents, as well as the monitoring of illegal substances and their presence or influence on an individual while driving, playing sports, or engaged in other regulated behaviors.

A "medical therapy" as used herein is intended to encompass any form of therapy with potential medical effect, including, without limitation, any pharmaceutical agent or treatment, compounds, biologics, medical device therapy, exercise, biofeedback or combinations thereof.

By "EEG data" we mean to include without limitation the raw time series, any spectral properties determined after Fourier transformation, any nonlinear properties after nonlinear analysis, any wavelet properties, any summary biometric variables and any combinations thereof.

A "sensory and cognitive challenge" as used herein is intended to encompass any form of sensory stimuli (to the five senses), cognitive challenges (to the mind), and other challenges (such as a respiratory $CO_2$ challenge, virtual reality balance challenge, hammer to knee reflex challenge, etc.).

A "sensory and cognitive challenge state" as used herein is intended to encompass any state of the brain and nervous system during the exposure to the sensory and cognitive challenge.

An "electronic system" as used herein is intended to encompass, without limitation, hardware, software, firmware, analog circuits, DC-coupled or AC-coupled circuits, digital circuits, FPGA, ASICS, visual displays, audio transducers, temperature transducers, olfactory and odor generators, or any combination of the above.

By "spectral bands" we mean without limitation the generally accepted definitions in the standard literature conventions such that the bands of the PSD are often separated into the Delta band ($f<4$ Hz), the Theta band ($4<f<7$ Hz), the Alpha band ($8<f<12$ Hz), the Beta band ($12<f<30$ Hz), and the Gamma band ($30<f<100$ Hz). The exact boundaries of these bands are subject to some interpretation and are not considered hard and fast to all practitioners in the field.

By "calibrating" we mean the process of putting known inputs into the system and adjusting internal gain, offset or other adjustable parameters in order to bring the system to a quantitative state of reproducibility.

By "conducting quality control" we mean conducting assessments of the system with known input signals and verifying that the output of the system is as expected. Moreover, verifying the output to known input reference signals constitutes a form of quality control which assures that the system was in good working order either before or just after a block of data was collected on a human subject.

By "biomarker" we mean an objective measure of a biological or physiological function or process.

By "biomarker features or metrics" we mean a variable, biomarker, metric or feature which characterizes some aspect of the raw underlying time series data. These terms are equivalent for a biomarker as an objective measure and can be used interchangeably.

By "non-invasively" we mean lacking the need to penetrate the skin or tissue of a human subject.

By "diagnosis" we mean any one of the multiple intended use of a diagnostic including to classify subjects in categorical groups, to aid in the diagnosis when used with other additional information, to screen at a high level where no a priori reason exists, to be used as a prognostic marker, to be used as a disease or injury progression marker, to be used as a treatment response marker or even as a treatment monitoring endpoint.

By "electronics module" or "EM" or "reusable electronic module" or "REM" or "multi-functional biosensor" or "MFB" we mean an electronics module or device that can be used to record biological signals from the same subject or multiple subjects at different times. By the same terms, we also mean a disposable electronics module that can be used once and thrown away which may be part of the future as miniaturization becomes more common place and costs of production are reduced. The electronics module can have only one sensing function or a multitude (more than one), where the latter (more than one) is more common. All of these terms are equivalent and do not limit the scope of the invention.

By "biosignals" we mean any direct or indirect biological signal measurement data streams which either directly derives from the human subject under assessment or indirectly derives from the human subject. Non-limiting examples for illustration purposes include EEG brainwave data recorded either directly from the scalp or contactless from the scalp, core temperature, physical motion or balance derived from body worn accelerometers, gyrometers, and magnetic compasses, the acoustic sound from a microphone to capture the voice of the individual, the stream of camera images from a front facing camera, the heart rate, heart rate variability and arterial oxygen from a would pulse oximeter, the skin conductance measured along the skin, the cognitive task information recorded as keyboard strokes, mouse clicks or touch screen events. There are many other biosignals to be recorded as well.

Non-Linear Stochastic Oscillator Algorithms

After one conducts artifact signal pre-processing, it is often of interest to process the raw time series data through any number of commonly used techniques. For instance, in the EEG literature, it is common to utilize time series analysis (Gabor), spectral analysis (Fast Fourier Transformation) and Non-linear dynamics analysis (Lyaponouv exponents, entropy, and dimensionality). In addition, a fruitful additional avenue of signal processing includes modeling with non-linear stochastic oscillators.

As a non-limiting example, an EEG signal is comprised of transient oscillations across a number of frequencies. Microphone recordings, accelerometer measurements and other biosignal data streams can be similarly analyzed. Decomposition of the EEG signal using a Fast Fourier transform (FFT) based power spectral approach continues to be a widely used analytic approach to extract features that can potentially aid with predicting AD or other disease state. General findings point to slowing of EEG in AD patients as measured by increased power in the lower frequency delta (1-4 Hz) and theta (4-8 Hz) sub-bands and decreased power in higher frequency sub-bands alpha (8-13 Hz) and beta (13-30 Hz).

Since EEG signals are non-stationary frequency based, methods such as FFT may not be effective tools for their analysis. Meanwhile, time domain nonlinear dynamics approaches are computationally complex and have not yet demonstrated reliable diagnostic power. A promising approach to EEG analysis is to model the biosignals using non-linear stochastic oscillators. Oscillator approaches have the advantage of using fewer parameters and capturing complex dynamics.

Clinical Study

The objective of this study was to identify the discriminant features of EEG signals extracted from Alzheimer's disease (AD) patients compared to healthy age-matched control subjects. The study design was an initial device, single visit parallel-group, multi-center trial. Up to 250 subjects were to get stratified into several cohorts. Inclusion criteria included: 1-healthy normal's ages; 2-diagnosis of probable AD according to the NINCDS-ADRDA Alzheimer's criteria; 3-Mini-mental state examination (MMSE) score 20-27; 4-diagnosis of mild cognitive impairment (MCI) according to Peterson criteria; 5-availability of a caregiver for AD and MCI subjects. Study exclusion criteria included: 1-diagnosis of significant neurological disease other than AD; 2-history of strokes, seizures, or traumatic brain injuries; 3-Chronic pain; and 4-use of high doses of sedating or narcotic medications. Other demographic items noted were date of birth, gender, ethnicity, education, relevant medical history, current prescription and non-prescription medications, nutritional supplements, and alcohol/tobacco use.

All Personal Health Information (PHI) was retained at Palm Drive Hospital and no PHI was provided to any collaborator for HIPAA Compliance. Subjects were assigned a random/sequential subject number which was the only identifier used to analyze the demographic, independent, and subsequently dependent variables of the study. All study data were encrypted via AES-256 bit encryption at the site of data acquisition before transport to central servers whenever any information was present in the data file. The inventors also employed a multi-step process whereby all parties remained blind until the final extracted EEG features data table was produced and circulated internally to the collaborating members.

Twenty six subjects were enrolled, one withdrew due to non-study related reasons, and one did not qualify as Alzheimer's disease (AD) or control (CTL) but was diagnosed with Mild Cognitive Impairment (MCI). Data from the remaining 24 subjects were considered, including 10 AD and 14 age-matched CTL. The subject information for these 24 individuals is presented in Table 1.

TABLE 1

Subject demographics and health information

| Subject No. | Gender | Age | Handedness | Clinical Diagnosis |
| --- | --- | --- | --- | --- |
| 1 | F | 57 | R | CTL |
| 2 | F | 86 | R | CTL |
| 3 | F | 54 | R | CTL |
| 4 | F | 68 | R | CTL |
| 5 | M | 63 | L | CTL |
| 6 | F | 83 | R | AD |
| 7 | F | 83 | R | CTL |
| 8 | F | 67 | R | CTL |
| 9 | M | 82 | R | AD |
| 10 | M | 69 | R | CTL |
| 11 | M | 75 | R | CTL |
| 12 | F | 74 | R | CTL |
| 13 | F | 75 | R | CTL |
| 14 | F | 57 | R | CTL |
| 15 | M | 81 | R | CTL |
| 16 | F | 85 | R | CTL |
| 17 | M | 84 | R | AD |
| 18 | F | 75 | R | AD |
| 19 | M | 80 | R | AD |
| 20 | M | 62 | R | AD |
| 21 | M | 73 | R | AD |
| 22 | M | 86 | R | AD |
| 23 | M | 76 | R | AD |
| 24 | F | 89 | R | AD |

Behavioral Tasks within the Battery of Assessment

Wearing the EEG headset data collecting device, subjects were asked to sit in a comfortable chair and open and close their eyes for nearly two-minute blocks, alternately recording 3 sessions of resting eyes-closed (EC) and 3 sessions of resting eyes-open (EO). They were then tasked with the four components of the CogState Research (Melbourne, Australia) brief battery: Detection, Identification, One Card Back, and One Card Learning tasks. CogState's brief battery is a computerized neuropsychological battery designed to be sensitive to the cognitive impairments that characterize mild-to-moderate Alzheimer's disease yet simple enough for patients to complete without requiring great support or assistance. The Detection task is a measure of simple reaction time and has been shown to provide a valid assessment of psychomotor function in healthy adults with schizophrenia. The Identification task is a measure of choice reaction time and has been shown to provide a valid assessment of visual attention. The One Card Learning and One Card Back cognitive tasks are valid measures of working memory.

Next, the Paced Auditory Serial-Addition Task (PASAT) task of 60 auditory addition trials was conducted at up to 3 different lag intervals of trial. PASAT is a measure of cognitive function that specifically assesses auditory information processing speed and flexibility, as well as calculation ability. Subjects are asked to listen to a series of numbers and are requested to add consecutive pairs of numbers as they listen. There is no visual component to this task.

Brief auditory binaural beat stimulations (90 seconds, 50-75 db) with differential beat frequencies of 6 Hz, 12 Hz, and 18 Hz were conducted next, followed by one final block of each resting EC and EO to close the data collection paradigm. There was normally a short break between recording sessions. Although there were a total of 18 possible recording tasks, a large number of subjects did not complete the PASAT 1.6 (s) interval (Task 13) and hence the data from this task was not included in the analysis.

EEG Signal Quality and Pre-Processing

The rechargeable battery powered Bluetooth enabled EEG headset eliminated frequently observed artifacts including line noise. However, it was critical to detect and eliminate other artifacts such as eye-blinks in the EEG signal. These artifacts, frequent at Fp1 location, often have high amplitudes relative to brain signals. Thus, even if their appearance in the EEG data is not frequent, they may bias the results of a given block of data or experiment. In this study, any DC offset of the EEG signal was subtracted and an artifact detection pre-processing algorithm was used to eliminate large amplitude artifacts greater than 4.5 standard deviations sigma. An algorithm was developed to detect such artifacts, nullify, and then reconstruct the nulled samples using FFT interpolation of the trailing and subsequent recorded data. However, amplitude-based artifact detection method sometimes fails to detect low frequency artifacts such as small eye blinks. Hence, the inventors recursively applied the artifact detection method to the modified signal up to three times. This method eliminated the remaining low frequency artifacts with very high reliability considering that the EEG signals are generally normally distributed (i.e., 1 in 49053 samples are expected to be out of range for the filtered signal while the sample size is in the 10000 to 20000 range). For illustrative purposes, FIG. 2 shows all the recorded EEG blocks concatenated one after the other for subject number 11, a CTL subject, in arbitrary units from the 10-bit analog-to-digital converter (ADC) before and after artifact detection. The enlarged area on the left is part of the second recording state EO2 where all eye blinks have been eliminated. The enlarged area on the right shows part of the 18 Hz auditory stimulation, AS3, where a few eye blinks plus a single artifact with large amplitude has been removed. The results show improvement over previous artifact detection. However, large amplitude signals in the PASAT recordings have not been filtered out due to larger during these sessions which are due normal physiological activities since subjects respond vocally.

The headset sample rate was specified at fs=128 Hz by the manufacturer. However, the effective sample rate was closer to fs=125 Hz in the experiments. Frequencies below 1 Hz and above 60 Hz (near Nyquist frequency) were filtered out. Furthermore, the inventors only analyzed frequencies between 2 Hz and 30 Hz due to the demonstrated reliability of the device.

Stochastic Oscillator Feature Extraction Algorithms

The signal processing method used to extract features from EEG traces and biosignals involves construction of a multi-parameter stochastic oscillator models. The aim is to adjust the parameters of the oscillator model to fit the essential characteristics of the EEG trace or biosignal time series.

A. Coupled Linear Oscillators

The first step in the process was to examine a set of coupled linear oscillators where the dynamical equation of a linear oscillator is given by (assuming unit mass values $m_1=m_2=\ldots=m_3=m_n=1$):

$$\ddot{x}+Kx=u\mu dW,$$

where x is the position of the oscillator mass, x-double dot is the acceleration of the mass, K is the linear stiffness matrix, u is the vector which only inputs the external driving force to the last mass (such that u=o for all masses but the last mass where it equals=1), mu is the noise intensity and dW is a vector-based Wiener process, representing the additive noise in the stochastic differential equation system. In trying to match the power spectrum from the oscillator model with the power spectrum from the EEG or biosignal times series, we were not able to get good concordance between the two without invoking at least ten (10) oscillators in the model and even then, the results were not very discriminatory. This led to the addition of non-linear terms to the model in an attempt to capture the non-linear dynamics observed in the EEG and biosignal time series.

B. Coupled Duffing Oscillators

The second step in the analytical process was to examine a set of coupled linear oscillators where the dynamical equation of a Duffing Oscillator is given by:

$$\ddot{x}+kx+bx^3=F(t)$$

where x is the position of the oscillator mass, k is the linear stiffness coefficient, b is the non-linear stiffness coefficient and F(t) represents the excitation or driving force. In trying to match the power spectrum from the oscillator model by optimizing the model parameters globally $\{k_1, k_2, b_1, b_2, mu\}$ to minimize the objective or error function J representing the difference in the frequency content between the power spectrum calculated from the EEG trace or biosignal times series and the model, we were able to get good concordance between the two spectra invoking only two (2) Duffing oscillators in the model. There was a significant improvement in the models ability to capture the essential frequency characteristics of the human EEG time series. In particular, the model was applied to N=10 Eyes Closed and N=10 Eyes Open time series and clear differences were observed in the model parameters between the two resting state conditions. Although promising, the frequency distributions were not sufficient to encourage us to examine EEG signals from Alzheimer's and control subjects.

C. Coupled Duffing-Van Der Pol Oscillators

Because of the non-linear features within the EEG traces and other biosignal time series of interest, the stochastic oscillator model is built off oscillators with non-linear terms and driven by white or stochastic noise. The inventors have chosen to add damping terms to the model and thus utilize the Duffing-van der Pol oscillator as the core element of the stochastic oscillator model. Recall that the dynamical equation of a single Duffing-van der Pol oscillator with damping is given by (again of unit mass where all $m_i=1$):

$$\ddot{x}+kx+bx^3-\epsilon\dot{x}(1-x^2)=F(t)$$

where x is the position of the oscillator, x-dot is the velocity, x-double dot is the acceleration, k is the linear stiffness coefficient, b is the non-linear stiffness coefficient, epsilon is the van der Pol damping coefficient, and F(t) represents external excitation or driving force. Parameter b indicates the strength of the Duffing nonlinearity resulting in multiple resonant frequencies. Parameter epsilon indicates the strength of van der Pol nonlinearity and determines the extent of self-excitation and the shape of the resulting limit cycle.

Figure 1:
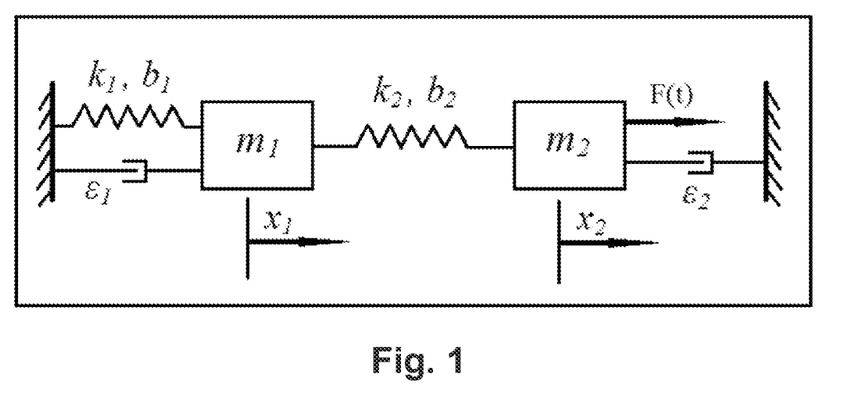
FIG. 1 is a schematic illustration of the coupled Duffing-van der Pol oscillators used to extract features from the bio-signal data streams, where $x_1$, $x_2$ are the positions of the first and second masses, $m_1$, $m_2$, $k_1$, $k_2$ are the linear spring stiffness constants, $b_1$, $b_2$ are non-linear spring stiffness constants, $epsilon_1$, $epsilon_2$ are the van der Pol damping coefficients, and $F(t)$ is the external excitation or driving force as a function of time applied to the second mass.
Figure 2A:
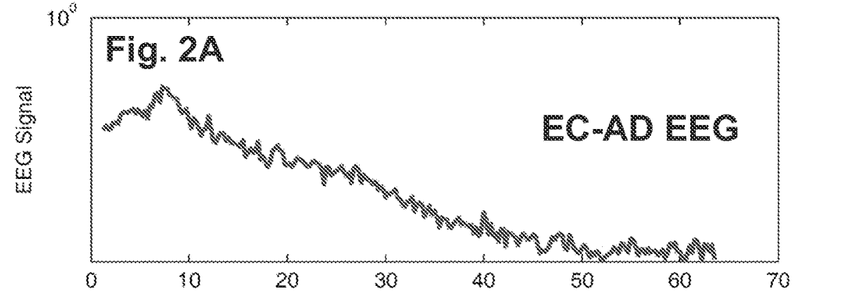
FIG. 2A is a graphical representation of the raw power spectrum of the EEG signal of an Alzheimer's disease subject during the resting Eyes Closed (EC) state.
Figure 2B:
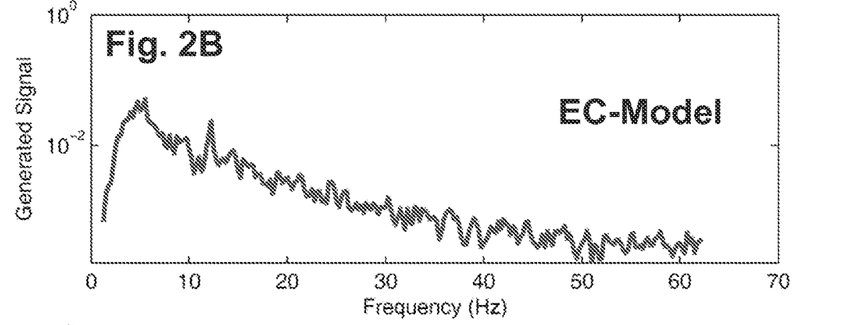
FIG. 2B is a graphical representation of the numerically synthesized power spectrum created from the results of fitting the stochastic model to the EEG of an Eyes Closed (EC) Alzheimer's subject.
Figure 2C:
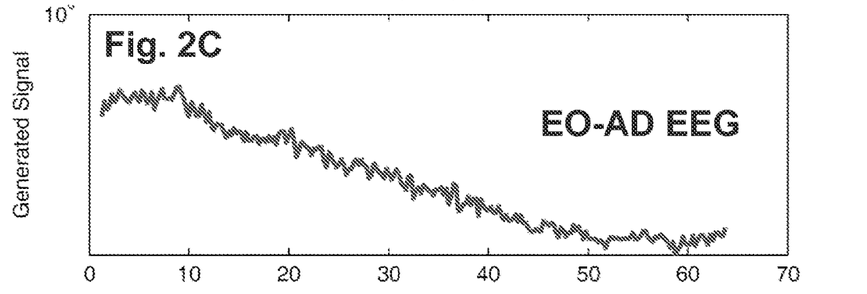
FIG. 2C is a graphical representation of the raw power spectrum of the EEG signal of an Alzheimer's disease subject during the resting Eyes Open (EO) state.
Figure 2D:
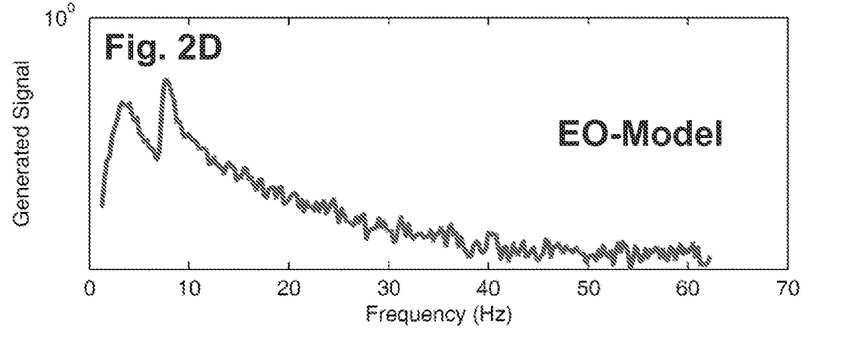
FIG. 2D is a graphical representation of the numerically synthesized power spectrum created from the results of fitting the stochastic model to the EEG of an Eyes Open (EO) Alzheimer's subject.

The present approach considers an array of coupled Duffing-van der Pol oscillators excited by white noise attached to the last oscillator: the schematic of which is shown in FIG. 1. For this work, we choose to use a system of two coupled Duffing-van der Pol oscillators as a non-limiting example to serve as a sufficiently accurate model to capture the power spectrum and nonlinear self-excited limit cycle behavior, information content, and complexity and predictability of the EEG signal or other generalized biosignal data stream. One could choose to use more than two Duffing-van der Pol oscillators in an analogous fashion, consistent and part of the present invention. The dynamical equations of the two Duffing-van der Pol oscillator model are:

$$\begin{cases} \ddot{x}_1 + k_1 x_1 + k_2(x_1 - x_2) + b_1 x_1^3 + b_2(x_1 - x_2)^3 - \epsilon_1 \dot{x}_1(1 - x_1^2) = 0. \\ \ddot{x}_2 - k_2(x_1 - x_2) - b_2(x_1 - x_2)^3 - \epsilon_2 \dot{x}_2(1 - x_2^2) = \mu dW. \end{cases}$$

where all variables and parameters for each mass were defined as above in the Duffing equation above with the refinement that $epsilon_1$ is the non-linear damping term for mass 1 ($m_1$) and $epsilon_2$ is the non-linear damping term for mass 2 ($m_2$), F(t)=mu*dW where mu represents the noise intensity (or amplitude) and dW as the distribution of frequencies within the driving force, which we take to be white noise with a flat or equal probability distribution across all frequencies. Thus this model is fit with a seven (7) parameter global fit which includes {$k_1$, $k_2$, $b_1$, $b_2$, $epsilon_1$, $epsilon_2$, mu}.

The signal processing method involves taking an individual time series of data from an EEG trace or other biosignal source, transforming it into its FFT power spectrum and then fitting the above 2 oscillator model (with seven adjustable parameters $k_1$, $k_2$, $b_1$, $b_2$, $epsilon_1$, $epsilon_2$, mu) in order to match the model via a global minimization method to three key characteristics of the biosignal times series: (i) the FFT power spectrum (distribution of frequencies) of the biosignal; (ii) the Shannon entropy or information content in the biosignal; and (iii) the Sample Entropy or predictability within the biosignal time series. The global optimization was initially evaluated by minimizing an objective error function J as a weighted average of the root mean square of the errors in power spectrum of each selected brain frequency bands shown in Table 2 and error in Shannon entropy. The initial optimization was formally presented as:

$$\min_P J = \sqrt{\sum_{j=1}^{m}(P_{E_j} - P_{O_j})^2} + w|S_E - S_O|.$$

Where J is the cost or error function, p represents the decision variables of the optimization, $P_{E_j}$ and $P_{O_j}$ are the frequency band powers of the normalized EEG signal and the model output, respectively, m represents the number of frequency bands (m=7), $S_E$ and $S_O$ represent the Shannon entropy of the EEG signal and the model output, respectively, w is a weighting factor and | . . . | represents the absolute value. However, the results from this analysis did not show as much accuracy as desired, so an improved objective function was assessed including an additional term for the Sample Entropy in addition to the Shannon Entropy. Thus, the preferred optimization is formally presented as:

$$\min_P J = \sqrt{\sum_{j=1}^{m}(P_{E_j} - P_{O_j})^2} + w_1|S_E - S_O| + w_2|SP_E - SP_O|.$$

where J is the cost or error function, p represents the decision variables of the optimization, $P_{E_j}$ and $P_{O_j}$ are the frequency band powers of the normalized EEG signal and the model output, respectively, m represents the number of frequency bands (m=7), $S_E$ and $S_O$ represent the Shannon entropy of the EEG signal and the model output, respectively, SPE and SPO represent the Sample Entropy of the EEG signal and the model output, respectively, w1 and w2 are weighting factors for Shannon and Sample entropy, respectively, and | . . . | represents the absolute value.

TABLE 2

Frequency ranges and corresponding major EEG frequency bands for use in the stochastic oscillator models.

| EEG Bands | Frequency Range ($H_z$) |
|---|---|
| $\delta_L$ | [1-2] |
| $\delta_U$ | [2-4] |
| $\theta$ | [4-8] |
| $\alpha$ | [8-13] |
| $\beta_L$ | [13-20] |
| $\beta_U$ | [20-30] |
| $\gamma$ | [30-60] |

Duffing-Van Der Pol Model Results for Healthy Normal Control Subjects

We used the EEG data from the same 40 EEG recordings (from N=20 subjects), with 20 under resting EC conditions and 20 under resting EO conditions. In each case, a global optimization routine based on a multi-start heuristic algorithm was used to match the output of the stochastic ODE models with the EEG signal by varying the model parameters including noise intensity as described above. Accordingly, the optimization was executed to match the frequency, information content, and complexity of the actual EEG signal with the output of the model. The mean (mu) and standard deviation (sigma) of the optimal values of model parameters for the 40 cases are presented in Table 3, categorized according to recording condition, either EC or EO.

Creation of a Stochastic Model to Discriminate Alzheimer's Disease EEG in EC or EO States In this section, the inventors will describe the stochastic Duffing-van der Pol oscillator model parameters for EEG recordings from AD patients under resting EC and EO conditions. The inventors match (i) the frequency content, (ii) loss of information, and (iii) signal complexity of the oscillator output with the EEG signal by simultaneously optimizing the model parameters and noise intensity. The inventors utilized EEG data from 20 EEG recordings, 10 under resting EC condition and 10 under resting EO condition from N=10 unique mild Alzheimer's subjects. The mean (mu) and standard deviation (sigma) of the optimal values of model parameters for the 10 cases are presented in Table 4. When looking at the Alzheimer's modeling results, it becomes clear that the EC state extracted features provide better discriminatory power than the EO state, as shown in Table 5.

Next one compares the EC and EO model parameters derived from the individual EEG traces between the two groups of control CTL and Alzheimer's disease AD subjects. The inventors initially used a univariate t-Test to assess False Positive Rate p-value significance. However, the normalcy test of the distribution of values revealed significant differences from normalcy so the non-parametric Wilcoxon rank sum test was also then employed. The results indicate that all model parameters for the Eyes Closed EC state are statistically different between CTL and AD subjects with the exception of the $b_2$ parameter in the t-Test (which is less relevant based on the normalcy criterion failure), as shown in Table 6. Moreover, the corresponding model parameter comparison for the EO state between AD and CTL were not statistically significant except $k_1$.

TABLE 3

Optimal parameters of the Duffing - van der Pol model (mean +/− standard deviation sigma) when discriminating EC and EO states in N = 20 healthy normal control subjects (T4.17).

| Parameter | Eyes-Closed (EC) | Eyes-Open (EO) |
|---|---|---|
| $k_1$ | 7286.5 ± 192.4 | 2427.2 ± 448.91 |
| $k_2$ | 4523.5 ± 282.3 | 499.92 ± 84.04 |
| $b_1$ | 232.05 ± 18.3 | 95.61 ± 24.20 |
| $b_2$ | 10.78 ± 2.3 | 103.36 ± 9.22 |
| $\epsilon_1$ | 33.60 ± 5.4 | 48.89 ± 9.49 |
| $\epsilon_2$ | 0.97 ± 0.19 | 28.75 ± 1.74 |
| $\mu$ | 2.34 ± 0.47 | 1.82 ± 0.78 |

TABLE 4

Optimal parameters of the Duffing - van der Pol oscillator (mean +/− standard deviation sigma) for EEG recordings from N = 10 Alzheimer's disease (AD) patients during resting EC and EO conditions (thesis T4.21).

| Parameter | Eyes-Closed (EC) | Eyes-Open (EO) |
|---|---|---|
| $k_1$ | 1742.1 ± 197.91 | 3139.9 ± 1,040.9 |
| $k_2$ | 1270.8 ± 277.13 | 650.32 ± 175.76 |
| $b_1$ | 771.99 ± 126.81 | 101.1 ± 27.86 |
| $b_2$ | 1.91 ± 0.22 | 81.3 ± 9.76 |
| $\epsilon_1$ | 63.7 ± 11.64 | 56.3 ± 5.75 |
| $\epsilon_2$ | 20.7 ± 5.64 | 19.12 ± 2.87 |
| $\mu$ | 1.78 ± 0.8 | 1.74 ± 0.67 |

Therefore, it appears based on these preliminary results in a small sample of N=10 Alzheimer's subjects that the coupled Duffing-van der Pol model applied to the Eyes Closed EC state EEG data can more easily distinguish the Alzheimer's disease subjects from the healthy normal controls.

TABLE 5

Power spectral comparison between actual EEG signals and simulated output of the Duffing-van der Pol model for the full set of EC and EO EEG traces of the N = 20 CTL (left) and N = 10 Alzheimer's disease (AD) subjects (right).

| Frequency Band | EEG signal EC | Generated Signal EC | EEG signal EO | General Signal EO |
|---|---|---|---|---|
| $\delta_L$ | 0.017 ± 0.012 | 0.0003 ± 0.000 | 0.047 ± 0.025 | 0.008 ± 0.005 |
| $\delta_U$ | 0.082 ± 0.037 | 0.005 ± 0.008 | 0.151 ± 0.045 | 0.117 ± 0.058 |
| $\theta$ | 0.200 ± 0.045 | 0.265 ± 0.083 | 0.272 ± 0.042 | 0.313 ± 0.074 |
| $\alpha$ | 0.490 ± 0.100 | 0.577 ± 0.056 | 0.226 ± 0.043 | 0.278 ± 0.058 |
| $\beta_L$ | 0.120 ± 0.034 | 0.078 ± 0.063 | 0.165 ± 0.036 | 0.127 ± 0.031 |
| $\beta_U$ | 0.048 ± 0.022 | 0.044 ± 0.011 | 0.100 ± 0.046 | 0.079 ± 0.033 |
| $\gamma$ | 0.018 ± 0.010 | 0.026 ± 0.007 | 0.034 ± 0.017 | 0.071 ± 0.042 |
| Shannon Entropy | 1.788 ± 0.079 | 1.92 ± 0.085 | 1.71 ± 0.112 | 1.571 ± 0.151 |
| Sample Entropy | 1.038 ± 0.203 | 1.17 ± 0.224 | 0.97 ± 0.197 | 1.198 ± .0177 |
| $\delta_L$ | 0.04 ± 0.025 | 0.0045 ± 0.003 | 0.043 ± 0.03 | 0.004 ± 0.001 |
| $\delta_U$ | 0.15 ± 0.044 | 0.120 ± 0.06 | 0.182 ± 0.07 | 0.091 ± 0.04 |
| $\theta$ | 0.40 ± 0.061 | 0.401 ± 0.06 | 0.332 ± 0.04 | 0.406 ± 0.07 |
| $\alpha$ | 0.21 ± 0.052 | 0.268 ± 0.07 | 0.225 ± 0.09 | 0.300 ± 0.03 |
| $\beta_L$ | 0.10 ± 0.023 | 0.105 ± 0.02 | 0.110 ± 0.02 | 0.100 ± 0.03 |
| $\beta_U$ | 0.05 ± 0.019 | 0.054 ± 0.01 | 0.077 ± 0.03 | 0.052 ± 0.02 |
| $\gamma$ | 0.02 ± 0.007 | 0.044 ± 0.02 | 0.025 ± 0.01 | 0.042 ± 0.01 |
| Shannon Entropy | 1.78 ± 0.039 | 1.70 ± 0.10 | 1.63 ± 0.32 | 1.62 ± 0.27 |
| Sample Entropy | 1.06 ± 0.19 | 1.17 ± 0.21 | 1.02 ± 0.39 | 1.29 ± 0.24 |

In an effort to understand the discriminatory power of the method, the inventors calculated the minimum required difference or effect size required to achieve a given statistical power with the variance and sample size in hand. The results of the power analysis can be seen in Table 7 below, where the effect size delta is shown at the 90%, 95%, 99% and 99.9% power.

TABLE 6

Statistical significance False Positive Rate p-value results for the comparison between model parameters extracted from EEG traces of Normal CTL (left) and AD (right) subjects using both the parametric t-Test and the non-parametric Wilcoxon rank sum test in both the Eyes Closed (EC) and Eyes Open (EO) states (T4.23).

| Parameter | t-test (EC) | Wilcoxon (EC) | t-test (EO) | Wilcoxon (EO) |
|---|---|---|---|---|
| $k_1$ | 1e−30 | 1e−5 | 0.013 | 0.027 |
| $k_2$ | 1e−23 | 1e−5 | 0.0034 | 0.0015 |
| $b_1$ | 1e−17 | 1e−5 | 0.58 | 0.027 |
| $b_2$ | 1e−12 | 1e−5 | 1e−6 | 1e−5 |
| $\in_1$ | 1e−10 | 1e−5 | 0.031 | 0.0018 |
| $\in_2$ | 1e−15 | 7e−6 | 4e−12 | 1e−5 |
| $\mu$ | 0.02 | 0.06 | 0.80 | 0.70 |

TABLE 7

Eyes Closed EC (left) and Eyes Open EO (right) power analysis to determine the minimum required difference between mean values for various power levels between CTL and AD subjects.

| Parameter | 90% | 95% | 99% | 99.9% |
|---|---|---|---|---|
| (EC) | | | | |
| $\Delta_{k1}$ (5,544.3) | 281.39 | 313.53 | 371.72 | 439.46 |
| $\Delta_{k2}$ (3,252.7) | 406.65 | 453.09 | 537.18 | 635.08 |
| $\Delta_{b1}$ (539.94) | 106.44 | 118.60 | 140.61 | 166.24 |
| $\Delta_{b2}$ (8.87) | 2.82 | 3.14 | 3.72 | 4.40 |
| $\Delta_{e1}$ (30.09) | 11.54 | 12.86 | 15.25 | 18.03 |
| $\Delta_{e2}$ (19.79) | 4.64 | 5.17 | 6.13 | 7.25 |
| $\Delta_{\mu}$ (0.56) | 0.87 | 0.97 | 1.15 | 1.36 |
| (EO) | | | | |
| $\Delta_{k1}$ (712.78) | 1,009.12 | 1,124.36 | 1,333.04 | 1,575.97 |
| $\Delta_{k2}$ (175.81) | 175.81 | 195.89 | 232.25 | 274.57 |
| $\Delta_{b1}$ (5.49) | 36.86 | 41.07 | 48.69 | 57.56 |
| $\Delta_{b2}$ (22.02) | 13.61 | 15.17 | 17.98 | 21.26 |
| $\Delta_{e1}$ (7.41) | 12.27 | 13.68 | 16.22 | 19.17 |
| $\Delta_{e2}$ (9.62) | 3.14 | 3.50 | 4.15 | 4.91 |
| $\Delta_{\mu}$ (0.07) | 1.08 | 1.21 | 1.43 | 1.70 |

In order to observe the quality of the correspondence between the model and the actual EEG traces, one can see in FIGS. 2A, 2B, 2C and 2D a comparison of the traces from human Alzheimer's subjects and the results of the non-linear stochastic model of the present invention.

EXAMPLES

While the above description contains many specifics, these specifics should not be construed as limitations on the scope of the invention, but merely as exemplifications of the disclosed embodiments. Those skilled in the art will envision many other possible variations that are within the scope of the invention. The following examples will be helpful to enable one skilled in the art to make, use, and practice the invention.

Example 1: Clinical Study and Data Collection

A. EEG Headset Characterization and Validation

A novel EEG headset device was modified for use in a clinical context to record a 128 samples/sec 10-bit data stream transmitted from the single EEG sensor placed at position Fp1 (based on a 10-20 electrode placement system). Differential voltage signals relative to the mastoid on the left ear were amplified via an application-specific integrated circuit (ASIC) containing an instrumentation differential amplifier followed by an analog filter with common mode rejection at 60 Hz. Two mastoid electrodes (reference and ground) were embedded in the left ear cup of the headset for compression contact to the left ear of the subject. After analog to digital conversion with a 10-bit unsigned analog-to-digital-converter (ADC), digital EEG signals passed through a digital signal processor before being transmitted via Bluetooth to a nearby computer.

Analytical bench studies verified the device achieving good signal-to-noise ratio. To compare the headset to traditional clinical EEG equipment, the inventors simultaneously recorded arbitrary waveform signals loaded into the buffer of a function generator hardwired in parallel to a Compumedics Neuroscan NuAmps system and the headset device. Publicly available reference EEG traces were uploaded into the Arb buffer and spooled out. After independent analysis of the recorded 10,000 samples/sec, 24-bit ADC signal from the Fp1 channel of the NuAmps system and the 128 samples/sec, 10-bit ADC output from the headset device, the gross spectral response was indistinguishable except for frequencies below 2 Hz. The analytical bench assessment demonstrated excellent ability to accurately record EEG signals in the 1-100 μV and 2-30 Hz ranges. The headset sample rate was specified at fs=128 Hz. However, the effective sample rate was closer to fs=125 Hz in the experiments. Frequencies below 1 Hz and above 60 Hz (near Nyquist frequency) were filtered out. However, the inventors only analyzed frequencies in the 2-30 Hz due to the headset device's demonstrated reliability.

The inventors investigated the integrity of EEG recordings by the device from human subjects. As the active electrode sits at position Fp1 just above the left eye on the forehead and mastoid, it was referenced via three surface contact electrodes on the left ear. The inventors recorded EEG signals sequentially from the same subject in both the resting eyes-closed (EC) and eyes-open (EO) conditions and computed the EC/EO ratio between the two power spectra. As expected, a statistically significant prominent peak of rhythm activity was observed centered around 10 Hz in the EC condition.

B. Behavioral Tasks and Clinical Study

The objective of this study was to identify the discriminant features of EEG signals extracted from Alzheimer's disease (AD) patients compared to healthy age-matched control subjects. Up to 250 subjects were to get stratified into several cohorts. Inclusion criteria included: 1-healthy normal's ages; 2-diagnosis of probable AD; 3-Mini-mental state examination; 4-diagnosis of MCI; 5-availability of a caregiver for AD and MCI subjects. Study exclusion criteria included: 1-diagnosis of significant neurological disease other than AD; 2-history of strokes, seizures, or traumatic brain injuries; 3-Chronic pain; and 4-use of high doses of sedating or narcotic medications. Other demographic items noted were date of birth, sex, ethnicity, education, relevant medical history, current prescription and non-prescription medications, nutritional supplements, and alcohol/tobacco use. All Personal Health Information (PHI) was retained at Palm Drive Hospital and no PHI was provided to any collaborator for HIPAA Compliance.

Twenty six subjects were selected, one withdrew and one did not qualify as Alzheimer's disease (AD) or control (CTL). Data from the remaining N=24 subjects were considered, including 10 AD and 14 age-matched CTL. There were 13 female and 11 male subjects with ages ranging from 57 to 89 years old. Wearing the device, subjects were asked to open and close their eyes for typically 90-second blocks, alternately recording 6 sessions under resting EC and EO conditions. They were then tasked with four components of the CogState Research (Melbourne, Australia) brief battery: Detection, Identification, One Card Back, and One Card Learning tasks. Next, the Paced Auditory Serial-Addition Task (PASAT) task of 60 auditory addition trials was conducted at up to 3 different lag intervals of trial. Brief auditory binaural beat stimulations (90 seconds, 50-75 db) with beat frequencies of 6 Hz, 12 Hz, and 18 Hz were conducted next, followed by two more blocks of resting EC and EO to close the data collection paradigm. Although there were a total of 18 possible recording tasks, a large number of subjects did not complete the PASAT 1.6 (s) interval (Task 13) and hence the data from this task was not included in the analysis.

C. EEG Signal Quality and Pre-Processing

The EEG device eliminated frequently observed artifacts including line noise. However, a novel artifact detection pre-processing algorithm was developed to eliminate eye blinks and other large amplitude artifacts greater than 4.5 sigma (standard deviation). The algorithm nullified and reconstructed the nulled samples using FFT interpolation of the trailing and subsequent recorded data. For illustrative purposes, FIG. 2 shows the recorded EEG block during EO4 for subject number 2, a CTL subject, in arbitrary units from the 10-bit analog-to-digital converter (ADC) before and after artifact detection where all artifacts (mainly eye blinks) have been eliminated.

The inventors calculate EEG features using five mother wavelets in order to overcome this a priori choice of mother wavelet consideration. In this study, the inventors applied five different CWT to EEG recordings from 10 AD patients and 14 healthy age matched CTL subjects during 17 different resting and active brain conditions. The inventors computed the absolute and relative geometric mean powers, standard deviations, skewness, wavelet entropy, and sample entropy of wavelet coefficients at scale ranges corresponding to the major brain frequency sub-bands, as features. A large number of discriminating features of AD patients were identified using the applied the nonparametric Wilcoxon rank-sum statistical testing method to a large number features and corrected for multiple comparisons through False Discovery Rate control test. Multivariate analysis of variance (ANOVA) was also applied to determine the degree of correlation between the features. Decision tree algorithms were then employed to classify the most significant EEG features of AD patients. Finally, the inventors developed a new index to choose most accurate discriminating EEG features of AD patients among those classified by different decision tree algorithms for the variety of utilized wavelet transforms based on statistical significance of the features and rate of false classification.

Example 2: Significant Stochastic Nonlinear Oscillator Features

As described earlier, traces from healthy control subjects in both the eyes closed (EC) and eyes open (EO) tasks were individual fit with the stochastic nonlinear oscillator (SNO) model (using the two coupled Duffing-van der Pol oscillators) for the 7 parameters $\{k_1, k_2, b_1, b_2, \text{epsilon}_1, \text{epsilon}_2, \text{mu}\}$ of the model and the average profile of each parameter and its standard deviation is reported (means with standard deviations sigma) in Table 3 as the Class Profile for CTL healthy control subjects. The same process of fitting individual EC and EO EEG traces from each of the N=10 Alzheimer's subjects individually for both EC and EO trace (means with standard deviations) is shown in Table 4 as the Class mean parameter profile for the Alzheimer's disease (AD) subjects. These two tables define the Class parameters that an unknown subject's stochastic nonlinear oscillator model results would be compared to. Other Class profiles for differential diagnosis and other disease and injury states are possible according to the present invention.

A. Univariate Statistics

Common statistical methods that rely on normal distribution were not fully met by these distributions. Therefore in addition to assessment via parametric t-Test, the inventors used the nonparametric Wilcoxon rank-sum test, which is the two sample version of the Kruskal-Wallis one-way analysis of variance (ANOVA) by ranks. The null hypothesis of the method is that the populations from which the samples originate have the same median. The test does not identify how many differences actually occur or where they occur.

The fit parameters from the stochastic nonlinear oscillator model fits to each individuals EEG trace in both the EC and EO state were then compared on a parameter by parameter basis (e.g. all the $b_1$ for the CTL subjects vs all the $b_1$ for the AD subjects) between the CTL and AD groups. The test results are shown to be statistically different between the two groups in each of the EC and EO tasks separately for each of the individual parameters of the stochastic nonlinear oscillator model. This is show in Table 6 for both the t-Test (where the normalcy assumption was not always met by the underlying distributions) and non-parametric Wilcoxon rank sum test across each of the seven fit parameters. Clearly the Wilcoxon results are very significant and therefore open the door to evaluate an unknown subject using the mean Class profile for each of CTL or AD in the future. From Table 6 and looking at the two Wilcoxon columns for the EC and EO task comparison, it appears from this limited sample that the Eyes Closed EC task is more discriminatory than the Eyes Open EO task. Further investigation is necessary.

The unknown subject would take a 1-2 minute recording of EEG in both the Eyes Closed and Eyes Open states, although the method of the invention can be expanded to include other tasks such as cognitive tasks, balance tasks, other biosensor data such as eye tracking, and accelerometer measurements for stability. The data would then be fit to the stochastic nonlinear oscillator model according to the methods of the present invention. The resulting seven parameter fit from the SNO model would then be compared to the healthy normal profile on a parameter by parameter basis (e.g. $k_1$ compared to the $k_1$ mean (standard deviation) for CTL subjects) and if the unknown subject's parameter (in this case $k_1$) fit within the 1 sigma (at 67% confidence interval) or 2 sigma (95% confidence interval) window of values, then it would heuristically classify the subject as a control. The same could be done with other groups of subjects including in the future Mild Cognitive Impairment (MCI) subjects, Parkinson's dementia, and other differential diagnosis groups for Alzheimer's disease like vascular dementia.

In the event that several parameters of the seven parameter set match the profile but some do not match for a given class of subjects, additional rules can be developed to make a best fit or a regression of the seven parameters to an index could weight with diagnostic probability. The easiest method is to look for the Class which has 4 or more parameters for which the unknown subject parameters fit within a Class set of parameters (i.e. where four is greater than 50% or the majority of the seven parameters). Alternatively, one could equally weight the seven parameters and measure the distance or closeness of an Unknown subject to the profile parameters of that Class by taking the sum of the distance from the central value of each parameter and adding them up. The small this summed distance is, the closer that individual would be to the Class profile of seven parameters. In this example, equal weights were placed across all seven parameters. In an alternate model, each distance could be normalized by the mean value of the parameter in the Class profile. Thus, the distance would be a relative measure from the profile mean, a sort of equally weighted z-score. Alternatively, differential weights could be assigned and each distance multiplied by that parameters weight to determine the distance to the Class profile.

As will be appreciated by those skilled in the art, the methods described herein may be implemented on a processor that executes software instructions for carrying out the methods described and claimed herein. The processor, in turn, may be implemented in a computer, a mainframe, a server, or the like. According to an example embodiment, the processor may be implemented with hardware components and/or software components such that the processor may be used to execute the steps of the method as described herein. For example, the hardware components may include a processor that is programmed to execute software that may collect bio-signal data from a subject as time series data extracted by, for example, an EEG device, extract features from the collected bio-signal data using a non-linear stochastic oscillator model to provide a series of summary fit parameters, and compare unknown fit parameters from the series of summary fit parameters to a set of normative fit parameters to determine whether the subject should be included in a group corresponding to the normative fit parameters or not as disclosed herein.

In an example embodiment, the processor that may be in operative communication with a memory component. The processor may include a standardized processor, a specialized processor, a microprocessor, or the like. The processor may execute instructions including, for example, instructions for implementing the steps of the methods as described herein. The memory component may store the instructions for execution by the processor. The memory component may include a tangible computer readable storage medium in the form of volatile and/or nonvolatile memory such as random access memory (RAM), read only memory (ROM, cache, flash memory, a hard disk, or any other suitable storage component. In one embodiment, the memory component may be a separate component in communication with the processor. According to another embodiment, the memory component may be integrated into the processor.

Those skilled in the art will appreciate that the invention may be applied to other applications and may be modified without departing from the scope of the invention. Accordingly, the scope of the invention is not intended to be limited to the exemplary embodiments described above, but only by the appended claims.

What is claimed:

1. A method for determining whether a subject should be included in a class of subjects having a disease or injury state by using non-linear stochastic oscillator classification, comprising the steps of:

collecting bio-signal data from the subject as time series data;

extracting features from the collected bio-signal data from the subject using a non-linear stochastic oscillator model to provide a set of subject summary fit parameters;

comparing the set of subject summary fit parameters to a set of normative fit parameters of the non-linear stochastic oscillator model defining the class of subjects having the disease or injury state to determine whether the subject should be included in the class of subjects corresponding to the set of normative fit parameters or not; and providing a treatment to the subject based on whether or not the subject is included in the class of subjects.

2. The method of claim 1, wherein the non-linear stochastic oscillator model is a Duffing-van der Pol oscillator model.

3. The method of claim 1, wherein collecting bio-signal data comprises capturing dynamics of EEG from the subject.

4. The method of claim 1, wherein the non-linear stochastic oscillator model comprises two coupled oscillators and the normative fit parameters correspond to values of linear spring stiffness constants k1 and k2, non-linear spring stiffness constants b1 and b2, damping coefficients epsilon1 and epsilon2, and noise intensity mu for the class of subjects.

5. The method of claim 1, wherein the class of subjects are at least one of healthy normal control subjects and a population of individuals having at least one of Alzheimer's disease, Parkinson's disease, Mild Cognitive Impairment, vascular dementia, schizophrenia, depression, multiple sclerosis, epilepsy, concussion, brain trauma, brain infections, and brain intoxications.

6. The method of claim 1, wherein determining whether the subject should be included in the class of subjects corresponding to the normative fit parameters or not comprises determining when the subject summary fit parameters are within a confidence interval of the normative fit parameters and, when so, then determining that the subject summary fit parameters are within a biological variation of normal for the normative fit parameters and, when not, then determining that the subject summary fit parameters are outside the normal biological variation for the normative fit parameters.

7. The method of claim 1, wherein when the subject summary fit parameters are determined to be a distance from the class of subjects, further comprising the step of creating distance signatures that are weighted equally across all the normative fit parameters defining the class of subjects.

8. The method of claim 1, wherein when the subject summary fit parameters are determined to be a distance from the class of subjects, further comprising the step of creating distance signatures that are not weighted equally across all the normative fit parameters defining the class of subjects.

9. The method of claim 1, wherein when the subject summary fit parameters are determined to be a distance from the class of subjects, further comprising the step of creating a distance signature that counts a number of subject summary fit parameters that are within the normative fit parameters defining the class of subjects.

10. A system that determines whether a subject has characteristics consistent with a normal state or an injury or disease state, comprising:

means for collecting bio-signal data;

a memory that stores software instructions; and a processor that processes the software instructions to implement a method including the steps of:

receiving from the collecting means bio-signal data of the subject as time series data;

extracting features from the collected bio-signal data from the subject using a non-linear stochastic oscillator model to provide a set of subject summary fit parameters;

comparing the set of subject summary fit parameters to a set of normative fit parameters of the non-linear stochastic oscillator model defining a class of subjects having the injury or disease state to determine whether the subject should be included in the class of subjects corresponding to the set of normative fit parameters or not; and providing an indication as to whether the subject is within or outside the class of subjects defined by the set of normative fit parameters whereby a medical treatment is provided to the subject based on whether the subject is within or outside the class of subjects defined by the normative fit parameters.

11. The system of claim 10, wherein the non-linear stochastic oscillator model is a Duffing-van der Pol oscillator model.

12. The system of claim 10, wherein the collecting means is an EEG device and the processor collects bio-signal data by capturing the dynamics of EEG from the subject using said EEG device.

13. The system of claim 10, wherein the non-linear stochastic oscillator model comprises two coupled oscillators and the normative fit parameters correspond to values of linear spring stiffness constants k1 and k2, non-linear spring stiffness constants b1 and b2, damping coefficients epsilon1 and epsilon2, and noise intensity mu for the class of subjects.

* * * * *